US011071690B2

(12) United States Patent
Garau Espinós

(10) Patent No.: US 11,071,690 B2
(45) Date of Patent: Jul. 27, 2021

(54) SEALED STERILE DEVICE FOR THE ASEPTIC SEPARATION AND CONCENTRATION OF BIOLOGICAL COMPONENTS

(71) Applicant: LABORATORIOS FIDIA FARMACEUTICA, S.L.U., Madrid (ES)

(72) Inventor: Guillermo Garau Espinós, Barcelona (ES)

( * ) Notice: Subject to any disclaimer, the term of this patent is extended or adjusted under 35 U.S.C. 154(b) by 301 days.

(21) Appl. No.: 16/468,131

(22) PCT Filed: Nov. 20, 2017

(86) PCT No.: PCT/ES2017/070768
§ 371 (c)(1),
(2) Date: Jun. 10, 2019

(87) PCT Pub. No.: WO2018/109246
PCT Pub. Date: Jun. 21, 2018

(65) Prior Publication Data
US 2020/0069521 A1 Mar. 5, 2020

(30) Foreign Application Priority Data
Dec. 16, 2016 (ES) ................ ES201631598

(51) Int. Cl.
*A61J 1/20* (2006.01)
*A61J 1/14* (2006.01)

(52) U.S. Cl.
CPC ........... *A61J 1/2086* (2015.05); *A61J 1/1412* (2013.01); *A61J 1/2096* (2013.01)

(58) Field of Classification Search
CPC ........ A61J 1/2086; A61J 1/1412; A61J 1/202; A61J 1/2037; A61J 1/2041; A61J 1/2096; B01L 2400/0478; B01L 3/50215
See application file for complete search history.

(56) References Cited

U.S. PATENT DOCUMENTS 3,735,900 A * 5/1973 Gores ............... A61M 5/284
222/129
4,644,807 A * 2/1987 Mar .................. G01N 30/18
141/27
(Continued)

FOREIGN PATENT DOCUMENTS

| EP | 2077115 A1 | 7/2009 |
| ES | 1059764 U | 6/2005 |
| ES | 2437541 A2 | 1/2014 |

OTHER PUBLICATIONS

English translation of International Search Report for PCT/ES2017/070768.
English translation of IPRP for PCT/ES2017/070768.

*Primary Examiner* — Timothy P. Kelly
(74) *Attorney, Agent, or Firm* — Egbert, McDaniel & Swartz, PLLC

(57) ABSTRACT

A sealed sterile device for the aseptic separation and concentration of biological components, which includes: a tube sealed at first end and which has a mouth at second end; a plunger of flexible material, without an actuation rod, installed inside the tube with the possibility of longitudinal movement, and which has a hole for charging with a fluid to be separated and concentrated and discharging the separated fractions, the hole being provide with a valved female Luer lock connection, the plunger also having a purging duct provided with a self-sealing filter for the automatic purging of the air/gas contained in the tube during the filling of the tube with the fluid to be separated and concentrated; and a cap for protecting the connection-plunger assembly, couplable to the mouth of the tube.

8 Claims, 3 Drawing Sheets

(56) References Cited

U.S. PATENT DOCUMENTS

| 6,849,052 B2 | 2/2005 | Uchigaki et al. |
| 2004/0251217 A1* | 12/2004 | Leach .................. B01L 3/5021 |
| | | 210/787 |
| 2011/0083978 A1 | 4/2011 | Lavi |
| 2014/0358033 A1 | 12/2014 | Lynn |

* cited by examiner

SEALED STERILE DEVICE FOR THE ASEPTIC SEPARATION AND CONCENTRATION OF BIOLOGICAL COMPONENTS

OBJECT OF THE INVENTION

The object of the present invention is a sealed and sterile device for the aseptic separation and concentration of biological components, such as blood, plasma, fat tissue, cells or any other.

This invention presents features aimed at allowing researchers, scientists, biologists, physicians and veterinarians to separate and concentrate different liquids, tissues or body fluids aseptically in a sealed device using density gradients and/or differential centrifugation, to be later analyzed, studied and applied "in vitro" and "in vivo" without problems of external/environmental contamination by pathogens, bacteria, etc.

FIELD OF APPLICATION OF THE INVENTION

This invention is applicable in those fields related to research R & D, biology, medicine and veterinary medicine.

STATE OF THE ART

Currently, there are several systems to separate and concentrate components of blood, tissues, bone marrow, etc., but they do not guarantee asepsis or possible contamination, because they are basically glass or plastic tubes with a cap (standard centrifuge, Eppendorf or Falcon tubes, as well as other tubes and devices available in the market) that separate some components; but, in order to remove said components from the tube, aspirating them by means of pipettes or cannulae, it is necessary to remove the cap from the tube, thus exposing the concentrate to the pathogens of the environment.

Other systems make it possible to fill the tubes and remove the fractions by means of needles that pierce a cap, usually made of rubber or silicone or flexible polymer, to inject or suck through them, with the danger that these needles pose for the manipulator/user of the device, besides the risk of contamination by inputs/outputs with the needles to the system.

Also, various devices for this application are known, such as those described in the utility model ES 1 059 764 U, or in the patent ES 2 437 541 B1, which have a syringe provided with a cylindrical body with both mouths at opposite ends and a plunger, without drive shaft, mounted with possibility of displacement inside said cylindrical body; thus doubling the possibility of contamination of the product contained in the syringe, due to the fact that it features two opposite entries.

Another drawback of the known devices is the difficulty of separately extracting the subsequent liquid fractions separated into layers, for example by centrifugation, without mixing them together.

DESCRIPTION OF THE INVENTION

The sealed and sterile device for the aseptic separation and concentration of biological components, object of the invention, features technical characteristics aimed at solving the mentioned problems and allowing the permeability to the inside of a separation tube through a valve mounted on a plunger closing the inside of the tube, without risks of contamination and safety for the user.

To this aim, the device comprises, at least:
a tube, sealed by a first end and having a mouth at a second end;
a plunger of flexible material, without drive shaft, mounted inside the tube with the possibility of longitudinal displacement and having a loading and unloading hole for a fluid to be concentrated and separated in various fractions, whose hole is provided with a female luer-lock valved connection; and a duct, fitted with a self-sealing filter, through which the automatic purge of the air/gas contained in the tube is made during the filling of the tube with the fluid to be separated and concentrated and,
a protection cap for the connection/plunger assembly, which can be attached to the mouth of the tube.

The plunger provided with the female luer-lock valved connection allows, by means of the coupling of a syringe with male luer-lock connection, to carry out the loading of the blood or liquid to be treated and the subsequent extraction of the obtained fractions after centrifugation through of the plunger and said valved female luer-lock connection, said operations are carried out in a safe, fast and reliable manner, as many times as necessary, without uncovering the tube and without using needles or other elements to pierce the plunger, thus avoiding contamination of the inside of the tube.

According to the invention, the plunger has a concave front end provided with radial fins in order to prevent turbulence and to enhance an accurate fractioning, controlling the fluid dynamics and stabilizing the passage of the liquid fraction separated from the inside of the cylinder to an extraction syringe coupled to the plunger connection.

Said plunger has a lateral surface with a perimetric recess defined between adjustment rings that ensure a good sealing of the inside of the tube while avoiding an excessive friction of the plunger with the tube.

According to the invention, the self-sealing plunger filter, arranged in the automatic air/gas purge duct, comprises a gelling filling which, once the tube is filled with the fluid to be separated, is automatically moistened with the fluid and immediately gels and seals, thus losing its permeability to air/gas and liquids, turning the whole device into a hermetically sealed chamber, so that the separated liquid fractions can only be removed through the female luer-lock connector of the plunger.

Therefore, this device does not use needles, thus avoiding risks for the user and risks of contamination.

Another advantage of this device is that the female luer-lock connection coupled to the plunger does not have gaps in its external part where significant fractions of the input or output fluids could be retained, and consequently being exposed to contamination.

However, in order to eliminate the risk of contamination due to this cause, the protective cap features an absorbent filler inside which externally protects and dries the female luer-lock connection from eventual drops of the fluids to be separated and concentrated, thus providing a permeability to the environment, and avoiding risks of contamination.

This cap provides a protection of the connection/plunger assembly which avoids contamination, by preventing its possible contact with any object during the handling of the tube by the user, and its contact with the particles in suspension displaced by the air currents that occur during the centrifugation of the contents of the tube.

A state-of-the-art lubricant is used in order to ensure a smooth sliding between the plunger and the tube cylinder.

In an embodiment of the invention, the device comprises a cylindrical buoy inside the tube, of a predetermined density, of a diameter suitable to the diameter of the inside of the tube and provided with a central hole with a unidirectional valve for the passage of the denser fractions towards the area below the buoy and floating over a denser fraction, although the starting position of the buoy is the lower end of the tube, and this buoy is very tight to the walls of the tube, but without being blocked in it; enough to slide and to stay stable without oscillations.

Said buoy is intended to be positioned by flotation between the fractions obtained after a centrifugation of the fluid to be separated forming a physical barrier between fractions of different density, floating above denser fractions.

In an embodiment of the invention, said buoy has a concave upper face abutting the central hole of fluid passage through the buoy.

In an embodiment of the invention, said buoy has on its upper face a perimeter chamfer facing a perimeter lip defined at the lower end of the plunger. The purpose of said perimeter chamfer is to cause a lateral expansion of said lip when the plunger contacts the buoy during the extraction of one of the separated fractions of liquid, causing an increase in friction between the plunger and the tube and, consequently, stopping the progress of the plunger.

These features make it easier to separately extract the separated fractions of liquid, avoiding their mixture during their extraction.

This device is designed to be used in centrifugation equipment that is the suitable size to insert it within, and features a software that, depending on the objective, can be separated and flexibly concentrate the fluid, from which (e. g. in the case of blood) more or less concentrated fractions, or of greater or lesser volume, can be removed.

DESCRIPTION OF THE FIGURES

In order to complement the description that is being made and in order to facilitate the understanding of the features of the invention, a set of drawings in which, the following has been represented with an illustrative and non-limiting character, is attached to the present specification.

PREFERRED EMBODIMENT OF THE INVENTION

Figures 1, 2:
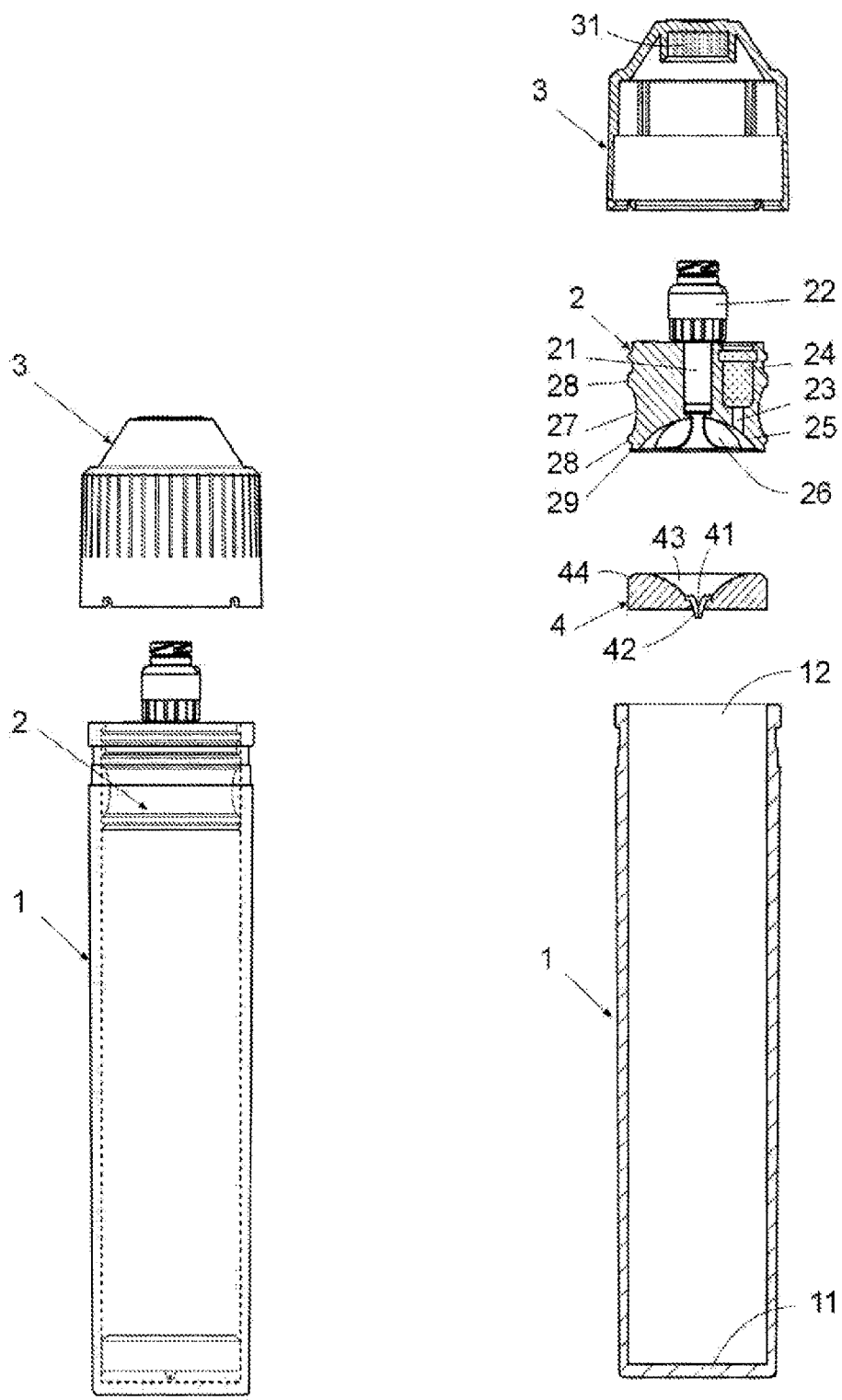
FIG. 1 shows an elevation view of an embodiment of the sealed and sterile device for separation of aseptic concentration of biological components, with the cap in the open position.
FIG. 2 shows an exploded elevation view in of the device of the previous figure, sectioned by a vertical plane.

As seen in FIG. 1, the sealed and sterile device for aseptic separation and concentration of biological components comprises a tube (1) with a first sealed end (11) and having a mouth (12) at a second end.

Inside the tube (1) a plunger (2) of flexible material, without a drive shaft, is mounted with the possibility of longitudinal movement.

Said plunger (2) has a hole (21) for loading a fluid to be separated and concentrated in various fractions, and for discharging the fractions of said fluid, of different density, separated by centrifugation.

The hole (21) has at the end facing the mouth (12) of the tube (1) a valved female luer-lock connection (22), whose valve is usually kept in a sealed position and opens when it is coupled with a male luer-lock connection (CM).

Figure 3:
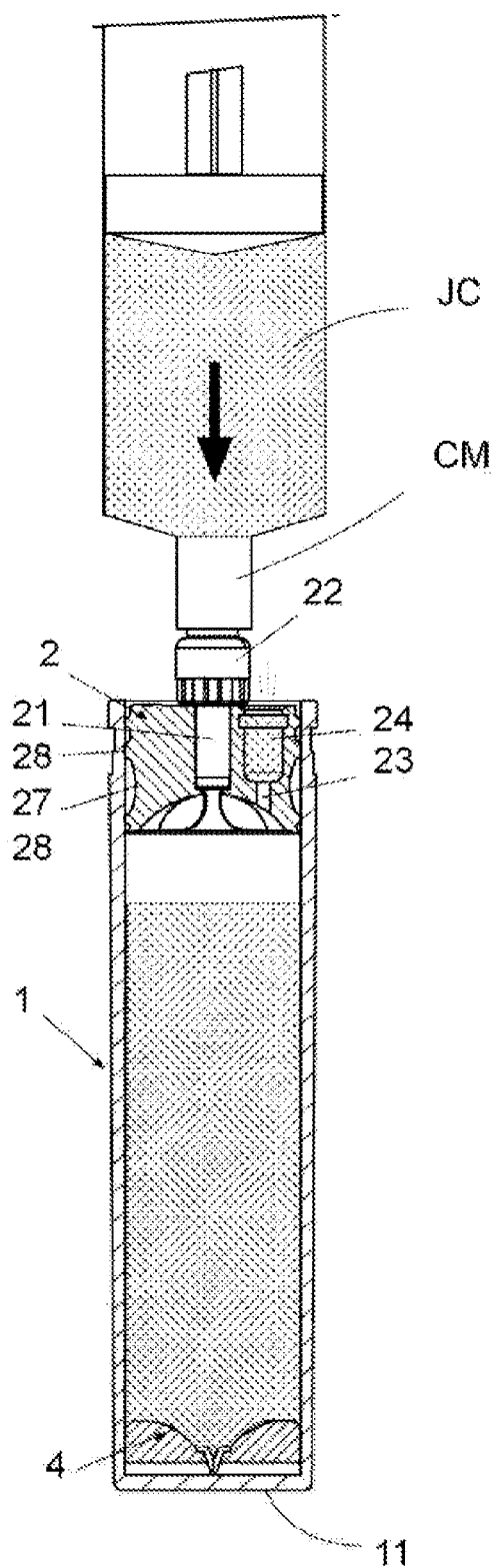
FIG. 3 shows an elevation view of the device of the previous figures during the loading of the fluid to be separated inside the tube by means of a loading syringe provided with a male "luer-lock" connection, complementary to the female "luer-lock" valved connection of the plunger, and coupled with it.

The plunger (2) also has a duct (23) for the automatic purging of the air/gas contained in the tube (1) during the filling of the tube (1) with the fluid to be separated and concentrated, this filling operation being carried out by means of a loading syringe (JC) provided with a male "luer-lock" connection (CM) complementary to that of the plunger (2), as shown in FIG. 3.

Said purge duct (23) is provided with a self-sealing filter (24) comprising a gelling filler which, when it comes into contact with the fluid to be separated due to the complete filling of the tube (1) and moistened with said fluid, gels and seals immediately, thus losing its permeability to air/gas and liquids.

Figure 5:
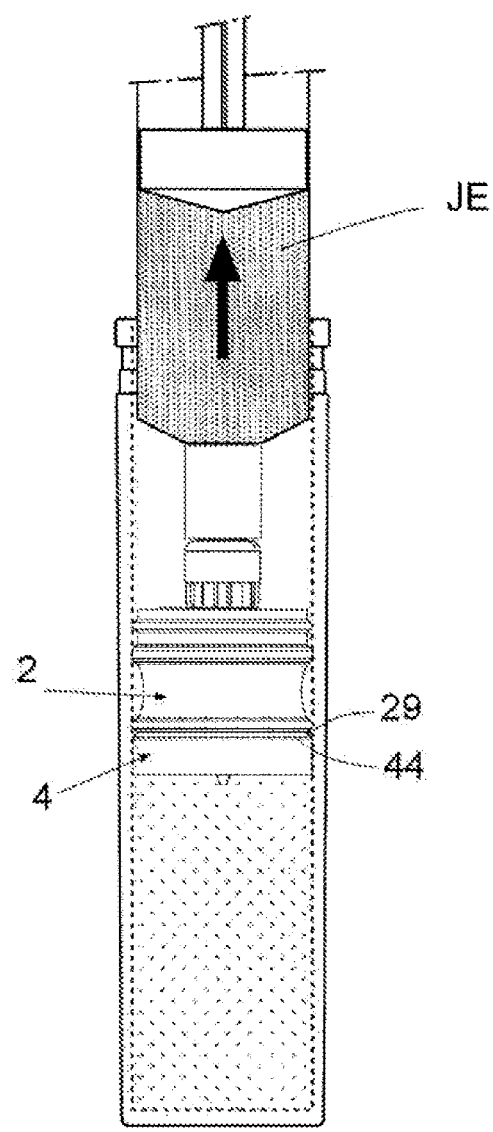
FIG. 5 shows a view of the device of the previous figures during the extraction of one of the fractions of liquid by means of an extraction syringe coupled to the luer-lock connection of the plunger, and said plunger contacting, by means of its perimeter lip, with the perimeter corner of the buoy.

The plunger (2) has a concave front end (25), oriented towards the first end (11) of the tube (1) and provided with radial fins (25), which prevent turbulence and favour a precise fractioning, stabilizing the passage of the liquid fraction separated from inside the tube (1) to an extraction syringe (JE) coupled to the female "luer-lock" valved connection (22) from the plunger (2) by means of a male "luer-lock" connection (CM) complementary, as shown in FIG. 5. This extraction syringe (JE) has a smaller diameter than the tube (1) acting in the coupling position as shaft of the plunger (2). The plunger has a perimeter recess (27) on its side surface defined between some adjustment rings (28) and the inside of the tube (1).

The device comprises a cap (3) for protecting the connection/plunger assembly, which can be coupled to the mouth (12) of the tube (1).

This protective cap (3) features an absorbent pad (31) inside it that protects and dries the female luer-lock connection (22) of the plunger (2) from possible drops of the fluids to be separated and concentrated, thus avoiding risks of contamination.

Figure 4:
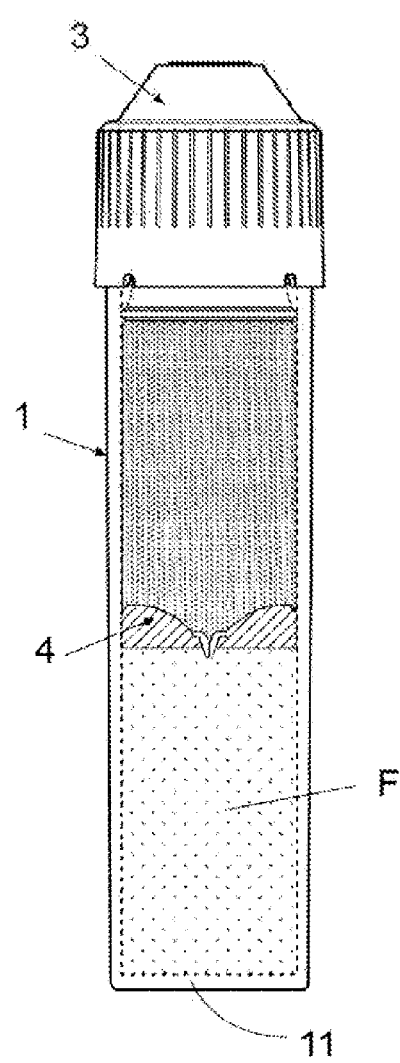
FIG. 4 shows a view of the device in the sealed position once centrifuged, featuring the buoy located between the two fractions of liquid of different density, separated and concentrated.

The device of the invention comprises a cylindrical plastic buoy (4) inside the tube (1), of a predetermined density and provided with a central hole (41) with a unidirectional valve (42) for the passage of the denser fractions towards the area below the buoy; said buoy forming a physical barrier between fractions of different density, once separated by centrifugation, as shown in FIG. 4.

Said buoy (4) has a concave upper face (43) that internally abuts the central hole (41) of fluid passage through the buoy (2) and, externally, in a perimeter chamfer (44).

The mission of this perimeter chamfer (44) is to cause a lateral expansion of the perimeter lip (29) of the plunger (2) and the braking of the advancement of the plunger (2) through the inside of the tube (1) when said plunger (2)

contacts the buoy (4) during the extraction of one of the separated fractions of liquid, as shown in FIG. 5.

In order to perform the extraction of the fraction of liquid located above the buoy (4) the plunger (2) is moved to the lower area, pushing it with the extraction syringe (JE) and keeping the stem of said extraction syringe free so that said shaft can move freely upward as the liquid fraction enters said syringe.

Once the nature of the invention has been sufficiently described, as well as a preferred embodiment, it is stated for the appropriate purposes that the materials, shape, size and arrangement of the described elements may be modified, provided that this does not entail an alteration of the essential features of the invention that are claimed below.

The invention claimed is:

1. A sealed and sterile device for aseptic separation and concentration of biological components, comprising:
    a tube sealed by a first end and having a mouth at a second end;
    a plunger of flexible material, without a drive shaft, mounted inside the tube with the possibility of and configured for longitudinal movement therein, the plunger having a hole for loading a fluid to be separated and concentrated, and for discharging the separated fractions, the hole is provided with a female luer-lock valved connection, and a purge duct, provided with a self-sealing filter, through which automatic purge of air/gas contained in the tube during the filling of the tube is carried out, with the fluid to be separated and concentrated; and
    a cap for protecting the plunger, which can be coupled to the mouth of the tube.

2. The device according to claim 1, wherein the plunger has a concave front end provided with radial fins, which prevent turbulence and stabilize passage of one of the separated liquid fractions from inside the cylinder to an extraction syringe coupled to the female luer-lock connection of the plunger.

3. The device according to claim 1, wherein the plunger has a side surface with a perimeter recess defined between some adjustment rings and the inside of the tube.

4. The device according to claim 1, wherein the self-sealing filter of the plunger, arranged in the duct for the automatic purging of the air/gas, comprises a gelling filler which, when in contact with the fluid to be separated, is moistened and it gels and seals immediately, thus losing its permeability to air/gas and liquids.

5. The device according to claim 1, wherein the cap features an absorbent filler inside, which protects and dries the female luer-lock connection from possible drops of the fluid to be separated and concentrated.

6. The device according to claim 1, further comprising within the tube, a cylindrical buoy of a predetermined density, of a diameter suitable for the diameter of the inside of the tube and provided with a central hole with a unidirectional valve for passage of denser fractions towards a zone located below the buoy; said buoy forming a physical barrier between liquid fractions of different density.

7. The device according to claim 6, wherein the buoy has a concave upper face that abuts the central hole of fluid passage through the buoy.

8. The device according to claim 6, wherein the buoy has a perimeter chamfer on its upper face facing a perimeter lip defined at a lower end of the plunger, the perimeter chamfer causes a lateral expansion of said perimeter lip and the stopping of the progress of the plunger when said plunger contacts the buoy during the extraction of one of the separated fractions of liquid.

* * * * *